(12) United States Patent
Brendel et al.

(10) Patent No.: US 10,275,859 B2
(45) Date of Patent: Apr. 30, 2019

(54) X-RAY IMAGING DEVICE FOR AN OBJECT

(71) Applicant: KONINKLIJKE PHILIPS N.V., Eindhoven (NL)

(72) Inventors: Bernhard Johannes Brendel, Norderstedt (DE); Gilad Shechter, Haifa (IL); Liran Goshen, Pardes-Hanna (IL); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/534,536

(22) PCT Filed: Sep. 14, 2016

(86) PCT No.: PCT/EP2016/071659
§ 371 (c)(1),
(2) Date: Jun. 9, 2017

(87) PCT Pub. No.: WO2017/046141
PCT Pub. Date: Mar. 23, 2017

(65) Prior Publication Data
US 2018/0204306 A1 Jul. 19, 2018

(30) Foreign Application Priority Data
Sep. 16, 2015 (EP) .................................. 15185492

(51) Int. Cl.
*G06K 9/00* (2006.01)
*G06T 5/00* (2006.01)
(Continued)

(52) U.S. Cl.
CPC .............. *G06T 5/002* (2013.01); *A61B 6/482* (2013.01); *A61B 6/5282* (2013.01); *G06T 5/50* (2013.01);
(Continued)

(58) Field of Classification Search
None
See application file for complete search history.

(56) References Cited

U.S. PATENT DOCUMENTS 8,009,890 B2 * 8/2011 Nishide ................. A61B 6/032
382/128
8,064,676 B2 11/2011 Li
(Continued)

FOREIGN PATENT DOCUMENTS

WO 1997001153 1/1997
WO 2012001648 1/2012
(Continued)

OTHER PUBLICATIONS

Richard, S., & Siewerdsen, J. H. (2008). Cascaded systems analysis of noise reduction algorithms in dual-energy imaging. Medical Physics, 35(2), 586-601. doi:10.1118/1.2826556.*
(Continued)

*Primary Examiner* — Feng Niu

(57) ABSTRACT

The invention relates to an X-ray imaging device (10) for an object, an X-ray imaging system (100) for an object, an X-ray imaging method for an object, and a computer program element for controlling such device or system and a computer readable medium having stored such computer program element. The X-ray imaging device (10) comprises a receiving unit (11) and a processing unit (12). The receiving unit (11) is configured to receive attenuation data representing attenuation properties of the object for at least two different X-ray spectra. The processing unit (12) is configured to decompose the attenuation data into decomposed data, to reduce noise in the decomposed data to obtain de-noised data, to back-convert the de-noised data into back-converted attenuation data, to combine back-converted attenuation data and the attenuation data into combined
(Continued)

attenuation data, and to decompose the combined attenuation data into combined decomposed data.

18 Claims, 4 Drawing Sheets

(51) Int. Cl.
*G06T 11/00* (2006.01)
*A61B 6/00* (2006.01)
*G06T 5/50* (2006.01)

(52) U.S. Cl.
CPC .. *G06T 11/005* (2013.01); *G06T 2207/10081* (2013.01); *G06T 2211/408* (2013.01)

(56) References Cited

U.S. PATENT DOCUMENTS

| | | | |
|---|---|---|---|
| 8,452,116 B1* | 5/2013 | Chuang | H04N 5/2351 382/260 |
| 8,548,216 B2 | 10/2013 | Raupach | |
| 9,036,771 B2* | 5/2015 | Yu | A61B 6/5258 378/19 |
| 9,600,866 B2* | 3/2017 | Brendel | G06T 5/002 |
| 2007/0076850 A1* | 4/2007 | Souchay | G21K 1/025 378/154 |
| 2008/0135789 A1 | 6/2008 | Du | |
| 2009/0257553 A1* | 10/2009 | Goto | A61B 6/032 378/19 |
| 2010/0220912 A1 | 9/2010 | Herbert | |
| 2010/0286525 A1 | 11/2010 | Osumi | |
| 2013/0329004 A1* | 12/2013 | Baqai | H04N 5/217 348/36 |
| 2014/0169653 A1 | 6/2014 | Maack | |
| 2014/0314331 A1* | 10/2014 | Zabic | G06T 5/002 382/254 |
| 2015/0004561 A1* | 1/2015 | Koehler | A61B 6/04 433/140 |
| 2015/0279005 A1* | 10/2015 | Brendel | G06T 5/002 382/131 |

FOREIGN PATENT DOCUMENTS

| | | | |
|---|---|---|---|
| WO | 2014/080311 | | 5/2014 |
| WO | 2014080311 | | 5/2014 |
| WO | WO/2014/080311 | * | 5/2014 |
| WO | 2015/028975 | | 3/2015 |
| WO | 2015074916 | | 5/2015 |

OTHER PUBLICATIONS

Zhao, et al., "Using Edge-Preserving Algorithm for Significantly Improved Image-Domain Material Decomposition in Dual Energy CT", The 13th International Meeting on Fully 3D Image Reconstruction in Radiology and Nuclear Medicine, May 31, 2015.

Schirra, et al., "Statistical Reconstruction of Material Decomposed Data in Spectral CT", IEEE Transactions on Medical maging, vol. 32, No. 7, Jul. 2013.

Li, et al., "Simultaneous Reduction in Noise and Cross-Contamination Artifacts for Dual-Energy X-Ray CT", Hindawi Publishing Corporation, BioMed Research International, vol. 2013, Article ID 417278.

Alvarez, et al., "Energy selective reconstructions in X-ray computerized tomography", Phys. Med. Biol. 21, pp. 733, (1976).

Brown, et al., "Acceleration of ML iterative algorithms for CT by the use of fast start images", Proc. SPIE 8313, (2012).

* cited by examiner

X-RAY IMAGING DEVICE FOR AN OBJECT

CROSS REFERENCE TO RELATED APPLICATIONS

This application is the U.S. National Phase application under 35 U.S.C. § 371 of International Application No. PCT/EP2016/071659, filed Sep. 14, 2016, published as WO 2017/046141 on Mar. 23, 2017, which claims the benefit of European Patent Application Number 15185492.4 filed Sep. 16, 2015. These applications are hereby incorporated by reference herein.

FIELD OF THE INVENTION

The invention relates to an X-ray imaging device for an object, an X-ray imaging system for an object, an X-ray imaging method for an object, and a computer program element for controlling such device or system and a computer readable medium having stored such computer program element.

BACKGROUND OF THE INVENTION

A CT scanner includes an X-ray tube that emits radiation that traverses an examination region and an object therein. A detector array located opposite the examination region across from the X-ray tube detects radiation that traverses the examination region and the object therein and generates projection data indicative of the examination region and the object therein. A reconstructor processes the projection data and reconstructs volumetric image data indicative of the examination region and the object therein.

In spectral or multi-energy CT, multiple attenuation projection data sets are acquired, which represent attenuation properties of a scanned object for different X-ray spectra. The multiple sets can be acquired through kVp switching, dual layer detectors, counting detectors, and/or otherwise. Each attenuation data set is acquired from a different spectral channel of the spectral or multi-energy CT system. Based on these multiple attenuation projection data sets, physical object properties can be determined, which is called material decomposition.

A possible approach for the material decomposition is decomposition in projection domain. For projection domain decomposition, the material decomposition is performed by converting attenuation line integrals of the different spectral channels into material line integrals. Due to a non-linearity of this material conversion, a bias is induced by noise in the attenuation line integrals (so-called noise induced bias). The strength of this bias directly depends on an amount of noise in the attenuation projection data sets. In many cases the bias will be unacceptably high, leading to strong deviations of reconstructed material images from a ground truth, thus preventing a reasonable quantitative evaluation for diagnostic purposes.

Thus, de-noising strategies are implemented to reduce noise in the attenuation line integrals, thus also reducing the bias in the decomposed material line integrals. Nevertheless, since an overly strong de-noising on the attenuation projection data sets leads to a loss of structures in the final images, some noise remains in the de-noised attenuation line integrals. Thus, there is still significant bias in the decomposed data. Furthermore, the remaining noise in the de-noised attenuation projection data still leads to severe noise in the decomposed data, since the decomposition is an ill-posed problem that strongly amplifies noise.

As a summary, the non-linearity of the material decomposition of a spectral or multi-energy CT system leads to noise induced bias, even if the noise on input data is reduced by de-noising. This bias leads to deviations of reconstructed material images from the ground truth, thus producing wrong values in quantitative evaluations for diagnostic purposes.

WO 2014/080311 A1 discloses an approach to reduce in the projection domain correlated noise from spectral/multi-energy projection data. This can be achieved based at least on variances of the material line integrals and a covariance there between.

SUMMARY OF THE INVENTION

There may be a need to provide an improved X-ray imaging device for an object, which allows a reduction of noise induced bias.

The problem of the present invention is solved by the subject-matters of the independent claims, wherein further embodiments are incorporated in the dependent claims. It should be noted that the aspects of the invention described in the following apply also to the X-ray imaging device, the X-ray imaging system, the X-ray imaging method, the computer program element, and the computer readable medium.

According to the present invention, an X-ray imaging device for an object is presented. The X-ray imaging device is configured to reduce noise in input data for a spectral decomposition. The X-ray imaging device comprises a receiving unit and a processing unit. The receiving unit is configured to receive attenuation data representing attenuation properties of the object for at least two different X-ray spectra. Based on these attenuation data, physical object properties can be determined (e.g. photoelectric effect, Compton scattering, water content, bone content, iodine content). The determination of these physical object properties is called material decomposition. For material decomposition, the processing unit is configured to decompose the attenuation data into decomposed data and to reduce noise in the decomposed data to obtain de-noised data. To reduce noise in the decomposed data to obtain de-noised data can be understood as decreasing the amount of noise or as eliminating noise. The processing unit is further configured to back-convert the de-noised data into back-converted attenuation data, wherein the back-conversion is the mathematical inverse of the decomposition. The processing unit is further configured to combine back-converted attenuation data and the attenuation data into combined attenuation data and to decompose the combined attenuation data into combined decomposed data by exactly the same decomposition as used for the conversion of attenuation data to decomposed data.

Thereby, the X-ray imaging device according to the inventions enables a noise reduction performed after a first decomposition of attenuation data into decomposed data and before a second decomposition of combined attenuation data into combined decomposed data. The latter or second decomposition after the noise reduction allows the noise reduction to directly contribute to a bias reduction. As a result, an improved X-ray imaging device for an object is provided, which allows an improved or increased reduction of noise induced bias.

In an example, the processing unit is configured to combine back-converted attenuation data and attenuation data into combined attenuation data by a selection and compilation of high spatial frequencies of the back-converted attenuation data and low spatial frequencies of the attenuation data. This example of the invention is based on the consideration that the noise removed by noise reduction has high spatial frequencies. Thus, if de-noised data is converted back into back-converted attenuation data, differences as compared to the de-noised data at high spatial frequencies are due to noise removed by the de-noising. Consequently, doing a "frequency-split", i.e., combining the high spatial frequencies of the back-converted attenuation data with the low spatial frequencies of the attenuation data results in data with less noise, and in consequence to less bias if this combined data is decomposed in the second decomposition into combined decomposed data. The frequency-split can be achieved by a high-pass filter and a low-pass filter.

The wording "to reduce noise in the decomposed data to obtain de-noised data" can be understood as partially decreasing the amount of noise or as fully eliminating noise. So, the terms "de-noising" and "reducing noise" are here used as synonyms. Additionally to its ability to reduce noise in the decomposed data to obtain de-noised data, the processing unit is configured in an example to reduce noise in the attenuation data before decomposition. This additional reduction of noise can be done before the first decomposition of attenuation data into decomposed data and/or before the second decomposition of combined attenuation data into combined decomposed data. As de-noising strategies to decrease the amount of noise or to eliminate noise e.g. a regularized maximum likelihood filter can be used. The de-noising strategies reduce noise in the attenuation line integrals, and are applied to each spectral channel separately. This noise reduction also reduces the bias in the decomposed material data. Since this de-noising is done before decomposition it is called pre-decomposition denoising (PDDN) in the following.

For material projection data, an anti-correlation filter (ACF) can be used as de-noising strategy, exploiting the anti-correlation of noise after decomposition. The ACF may filter anti-correlated noise from decomposed material data using a statistical model. An example of a suitable anti-correlation filter comprises a regularized maximum likelihood filter that includes a data term and a regularization term. The regularization term may include two or more sub-terms, one for each material.

Above example that the processing unit is configured to combine back-converted attenuation data and attenuation data into combined attenuation data by a selection and compilation of high spatial frequencies of the back-converted attenuation data and low spatial frequencies of the attenuation data can be further specified by the use of both, PDDN and ACF, separately, to reduce noise in the decomposed data to obtain PDDN de-noised data as well as ACF de-noised data. So based on the assumption that noise removed by ACF has high spatial frequencies, ACF de-noised data is converted back to back-converted attenuation domain. It is then expected that differences as compared to PDDN de-noised data at high spatial frequencies are due to noise removed by ACF. Consequently, doing a "frequency-split", i.e., combining high spatial frequencies of back-converted ACF de-noised or processed data with the low spatial frequencies of PDDN de-noised or processed data results in data with less noise, and in consequence with less bias if these combined attenuation data is decomposed in the second decomposition into combined decomposed data. Above assumption that noise removed by ACF has high spatial frequencies is a good assumption due to the properties of the applied regularization term, which evaluates only differences between directly neighboring detector pixels.

Two possible approaches for the material decomposition (determining physical object properties) are decomposition in image domain and decomposition in projection domain. For image domain decomposition, an attenuation image is reconstructed for each acquired attenuation data set, and the material decomposition is performed on the reconstructed attenuation images, converting the reconstructed attenuation values for one image location into material values. For projection domain decomposition, the material decomposition is performed by converting attenuation line integrals of the different spectral channels into material line integrals.

Several combinations of decomposition and de-noising in projection domain and image domain are possible. In the following, some possibilities are first mentioned and then, some possible combinations are explained in more detail. In an example, the processing unit is configured to decompose in projection domain, whereby the attenuation data represent attenuation line integrals, and the processing unit is configured to decompose the attenuation line integrals into decomposed data representing decomposed line integrals. In other words, material decomposition is performed in projection domain by converting attenuation line integrals of the different spectral channels into decomposed material line integrals. In an example, the processing unit is configured to decompose in image domain, whereby the attenuation data represents attenuation images, and the processing unit is configured to decompose the attenuation images into decomposed data representing decomposed images.

In an example, the processing unit is configured to reduce noise in image domain, whereby the processing unit is configured to reduce noise in the decomposed images to obtain de-noised data representing de-noised images. In an example, the processing unit is configured to reduce noise in projection domain, whereby the processing unit is configured to reduce noise in the decomposed line integral data to obtain de-noised data representing de-noised line integrals. In an example, the processing unit is configured to reduce noise in projection domain and in image domain, whereby the noise reduction contains forward-projections and back-projection to switch between projection domain and image domain, and to reduce noise in the decomposed line integrals either in image domain or in projection domain or in both domains to obtain decomposed data representing decomposed line integrals.

In more detail to the last two passages, at least the following combinations of decomposition and de-noising in projection domain and image domain are possible:

Decomposition and de-noising in projection domain, which means attenuation line integral data are first decomposed into decomposed line integral data, then noise is reduced in projection domain, back-conversion is done in projection domain, combination is done in projection domain, and the second decomposition is done in projection domain. Further, a reconstruction of images is possible. Reconstruction means a generation of volumetric image data, including material volumetric image data.

Decomposition and de-noising in image domain, which means attenuation line integral data are first reconstructed to attenuation image data, then decomposed into decomposed image data, noise is reduced in image domain, back-conversion is done in image domain, combination is done in image domain, and the second decomposition is done in image domain.

Decomposition in projection domain and de-noising in image domain, which means attenuation line integral data are first decomposed into decomposed line integral data, then reconstructed into decomposed image data, noise is reduced in image domain, back-conversion is done by a combination of forward projection to convert images to projection domain and the mathematical inverse of the decomposition to convert from material domain to attenuation domain, combination is done in projection domain, and the second decomposition is done in projection domain. Further, a reconstruction of images is possible.

Decomposition in projection domain and de-noising in projection domain and in image domain, which means attenuation line integral data are first decomposed into decomposed line integral data, then noise reduced in projection domain, reconstructed into decomposed image data, noise is reduced in image domain, back-conversion is done by a combination of forward projection to convert images to projection domain and the mathematical inverse of the decomposition to convert from material domain to attenuation domain, combination is done in projection domain, and the second decomposition in projection domain. Further, a reconstruction of images is possible. Alternatively to do separate de-noising in projection domain and image domain with a reconstruction in between, a regularized statistical iterative reconstruction can be done to generate denoised decomposed images from decomposed line integral data.

According to the present invention, also an X-ray imaging system for an object is presented. The X-ray imaging system comprises an X-ray detector and the X-ray imaging device as described above. The X-ray detector provides the attenuation data received by the X-ray imaging device. The X-ray imaging device comprises a receiving unit and a processing unit. The receiving unit is configured to receive attenuation data representing attenuation properties of the object for at least two different X-ray spectra. The processing unit can be configured to combine back-converted attenuation data and attenuation data into combined attenuation data by a selection and compilation of high spatial frequencies of the back-converted attenuation data and low spatial frequencies of the attenuation data. As de-noising strategies to decrease the amount of noise or to eliminate noise PDDN, ACF and the like can be used.

According to the present invention, also an X-ray imaging method for an object is presented. It comprises the following steps, not necessarily in this order:

receiving attenuation data representing attenuation properties of the object for at least two different X-ray spectra,
decomposing the attenuation data into decomposed data,
reducing noise in the decomposed data to obtain de-noised data,
back-converting the de-noised data into back-converted attenuation data,
combining back-converted attenuation data and attenuation data into combined attenuation data, and
decomposing the combined attenuation data into combined decomposed data.

Based on the assumption that noise removed by ACF as de-noising strategy has high spatial frequencies, ACF de-noised data can be converted back to back-converted attenuation domain. Differences compared to PDDN de-noised data at high spatial frequencies are due to noise removed by ACF. Consequently, doing a "frequency-split", i.e., combining high spatial frequencies of back-converted ACF de-noised data with the low spatial frequencies of PDDN de-noised data results in data with less noise, and in consequence with less bias when these combined attenuation data is decomposed in the second decomposition into combined decomposed data.

According to the present invention, also a computer program element is presented, wherein the computer program element comprises program code means for causing an X-ray imaging device as defined in the independent device claim to carry out the steps of the X-ray imaging method when the computer program is run on a computer controlling the X-ray imaging device.

It shall be understood that the X-ray imaging device, the X-ray imaging system, the X-ray imaging method, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
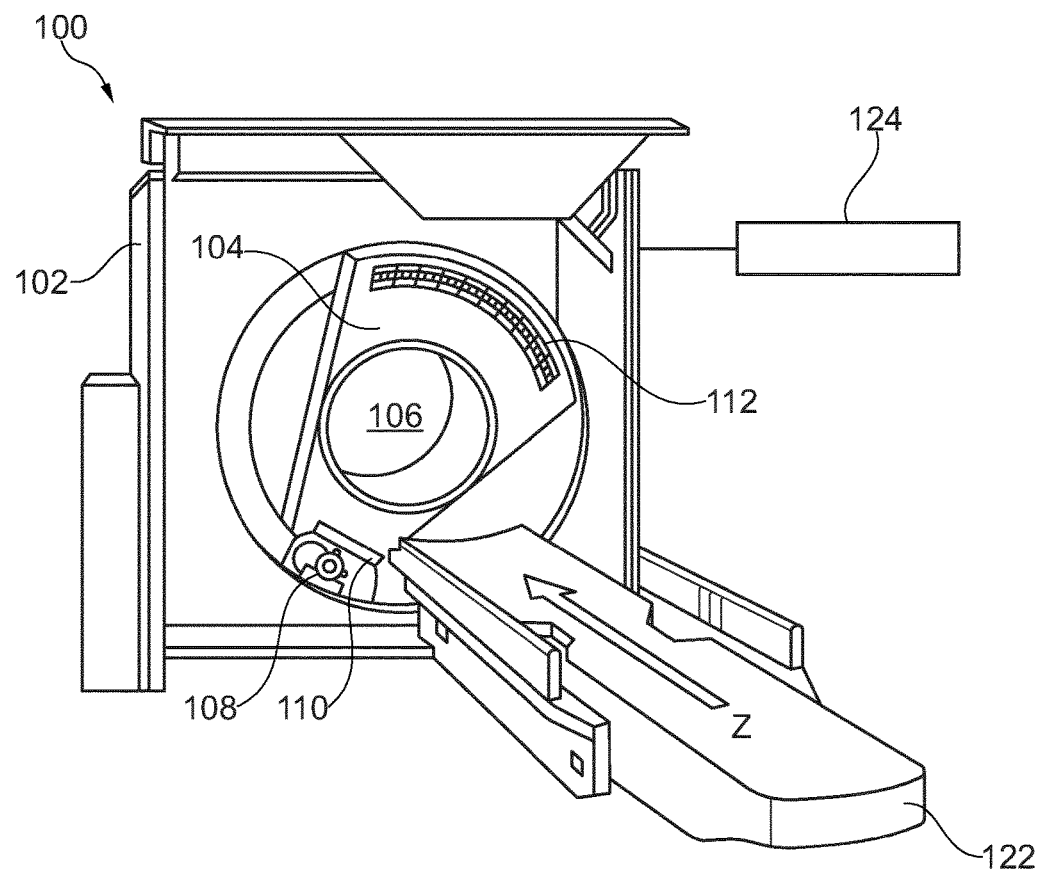
FIG. 1 shows schematically and exemplarily an embodiment of an X-ray imaging system according to the invention.

FIG. 1 shows schematically and exemplarily an embodiment of an X-ray imaging system 100 according to the invention. The imaging system 100, such as a computed tomography (CT) scanner, includes a generally stationary gantry 102 and a rotating gantry 104. The rotating gantry 104 is rotatably supported by the stationary gantry 102 and rotates around an examination region 106 about a longitudinal or z-axis.

A radiation source 108, such as an X-ray tube, is rotatably supported by the rotating gantry 104. The radiation source 108 rotates with the rotating gantry 104 and emits radiation that traverses the examination region 106. A source collimator 110 includes collimation members that collimate the radiation to form a generally cone, wedge, fan or other shaped radiation beam.

A radiation sensitive detector array 112 subtends an angular arc opposite the radiation source 108 across the examination region 106. The detector array 112 includes one or more rows of detectors that extend along the z-axis direction. The detector array 112 detects radiation traversing the examination region 106 and generates projection or attenuation data (or measured line integrals) indicative thereof.

The projection data is spectral projection data and includes at least two sub-sets of projection data, each representing attenuation properties of the scanned object for different X-ray spectra. Such projection data can be obtained where the detector array 112 includes a photon counting detector and/or a multi-layer spectral detector, and/or the radiation source 108 is configured to switch between at least two different energy spectrums during a scan.

A patient support 122, such as a couch, supports an object or subject such as a human patient in the examination region 106.

A computing system or computer serves as an operator console 124, which allows an operator to control an operation of the system 100, such as selecting and/or activating at least a projection domain de-noising algorithm.

Figure 2:
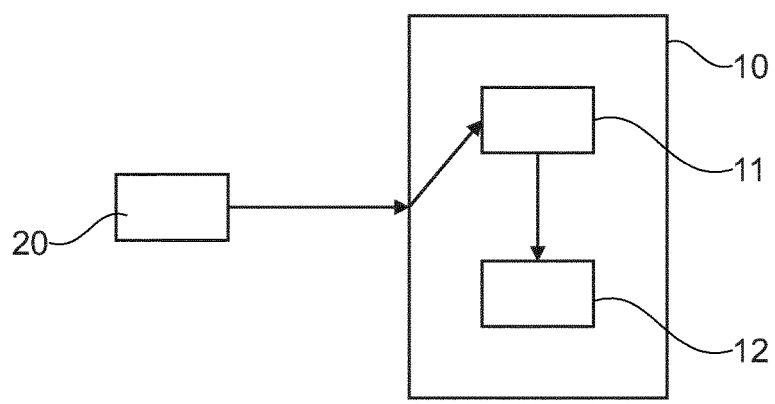
FIG. 2 shows schematically and exemplarily an embodiment of an X-ray detector and the X-ray imaging device according to the invention.

FIG. 2 shows schematically and exemplarily an embodiment of an X-ray detector 20 and an X-ray imaging device 10 according to the invention. The X-ray imaging device 10 and the X-ray detector 20 are part of the X-ray imaging system 100. The X-ray detector 20 comprises the radiation sensitive detector array 112 and provides attenuation data to be received by the X-ray imaging device 10. The X-ray imaging device 10 comprises a receiving unit 11 and a processing unit 12. The receiving unit 11 receives attenuation data representing attenuation properties of the object for at least two different X-ray spectra. The processing unit 12 decomposes the attenuation data into decomposed data, reduces noise in the decomposed data to obtain de-noised data, back-converts the de-noised data into back-converted attenuation data, combines back-converted attenuation data and the attenuation data into combined attenuation data, and decomposes the combined attenuation data into combined decomposed data. These steps are explained below in further detail.

The X-ray imaging device 10 according to the inventions enables a noise reduction performed after a first decomposition of attenuation data into decomposed data and before a second decomposition of combined attenuation data into combined decomposed data. The latter or second decomposition after the noise reduction allows the noise reduction to directly contribute to a bias reduction. As a result, an improved X-ray imaging device 10 for an object is provided, which allows an improved or increased reduction of noise induced bias.

The wording "to reduce noise in the decomposed data to obtain de-noised data" can be understood as partially decreasing the amount of noise or as fully eliminating noise. So, the terms "de-noising" and "reducing noise" are here used as synonyms. A reduction of noise can be done before the first decomposition of attenuation data into decomposed data and/or before the second decomposition of combined attenuation data into combined decomposed data. As de-noising strategies to decrease the amount of noise or to eliminate noise e.g. PDDN and/or an anti-correlation filter (ACF) can be used.

Two possible approaches for the material decomposition (determining local physical object properties) are decomposition in image domain and decomposition in projection domain. The same applies for noise reduction. It can be done in image domain and in projection domain. Using and combining these approaches, at least the following options are available:

The processing unit 12 may decompose in projection domain, whereby the attenuation data represent attenuation line integrals, and the processing unit 12 decomposes the attenuation line integrals into decomposed data representing decomposed line integrals.

The processing unit 12 may decompose in image domain, whereby the attenuation data represents attenuation images, and the processing unit 12 decomposes the attenuation images into decomposed data representing decomposed images.

The processing unit 12 may reduce noise in image domain, whereby the processing unit 12 reduces noise in the decomposed images to obtain de-noised data representing de-noised images.

The processing unit 12 may reduce noise in projection domain, whereby the processing unit 12 reduced noise in the decomposed line integral data to obtain de-noised data representing de-noised line integrals.

The processing unit 12 may reduce noise in projection domain and in image domain, whereby the noise reduction contains forward-projections and back-projection to switch between projection domain and image domain, and to reduce noise in the decomposed line integrals either in image domain or in projection domain or in both domains to obtain decomposed data representing decomposed line integrals.

All spectral CT applications that offer quantitative imaging, as e.g. virtual mono-energetic images at low energies, virtual non-contrast images, iodine maps, iodine to calcium classification and many others may benefit from reducing noise before decomposition. Reduced noise leads to reduced bias induced by the noise and therefore to more accurate virtual monochromatic images, iodine maps, virtual no contrast images, etc. To reduce noise before decomposition, two independent ideas for filtering out unnecessary high frequencies before decomposition may be used individually or combined.

A. Performing reconstruction x- and z-low-pass filtering that balance between sharpness and de-noising in a single-energy CT image before decomposition.

B. Understanding that an object dependent noise induced bias distortion contains different frequencies within an image domain, decomposed sonograms may be split into a few frequency ranges. For each range, frequencies are pre-filtered out that are higher from this frequency range, and then the pre-filtered frequencies are decomposed separately for each frequency range.

Both above explained ideas A and B, i.e. pre-filtering and split to frequency bands can be performed alone. As explained in the following, both ideas A and B can also be combined.

To simplify the notations of the method that is applicable for a multi-energy CT, it is assumed by an example a dual energy CT, where low/high-energy line integrals (preps) $p_{l/h}$, are decomposed to photo/scatter preps. Following the principle of filtering out unnecessary frequencies before decomposition, first N different 2D low-pass filters are applied on the preps $p_{l/h}$ denoted by $LP_n(\vec{k})$, where $\vec{k}=(k_x,k_z)$ and $n \in [1:N]$. The low-pass filters $LP_n(\vec{k})$ are given according to (1) below.

$$LP_n(\vec{k})=(X_{flt}*Z_{flt}*F_n)(\vec{k}). \tag{1}$$

Here, $X_{flt}$ and $Z_{flt}$ are x- and z-low-pass filters that balance between sharpness and de-noising in the single-energy CT image. The x-filtering kernel performed along a detector arc is multiplied by a ramp filter during a convolution step, and z-filtering, where z is a gantry rotation axis, defines a reconstructed image slice width. For n∈[1: N−1], the kernels $F_n(\vec{k})$ in (1) are a series of 2D low-pass filters, while for n=N, $F_{n=N}(\vec{k})=1$ for all $\hat{k}$, see the following rules.

$$F_{n=1}(\vec{k}) \in [0\ 1]\ (a)$$

$$F_{1<n<N}(\vec{k}) = \begin{cases} F_{n-1}(\vec{k}) > 0 & 1 \\ F_{n-1}(\vec{k}) = 0 & \in [0\ 1] \end{cases} (b) \quad (2)$$

$$F_{n=N}(\vec{k}) = 1\ (c).$$

For each channel", the sonograms pre-filtered by $LP_n(\vec{k})$ are decomposed and then a band-pass filter is applied on each channel denoted by $BP_n(\vec{k})$ in the following way.

$$BP_{n=1}(\vec{k})=1 \quad (a)$$

$$BP_{n>1}(\vec{k})=F_n(\vec{k})-F_{n-1}(\vec{k}) \quad (b).$$

Figure 3:
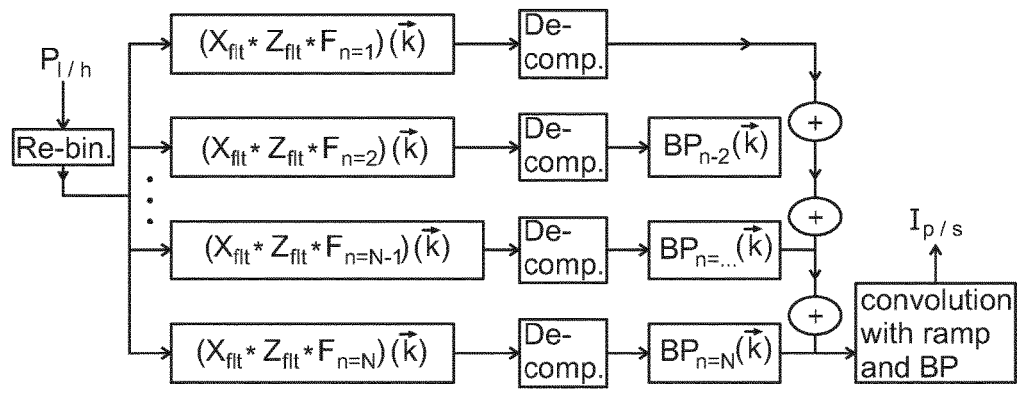
FIG. 3 shows a flow-chart of an embodiment according to the invention.
Figure 4:
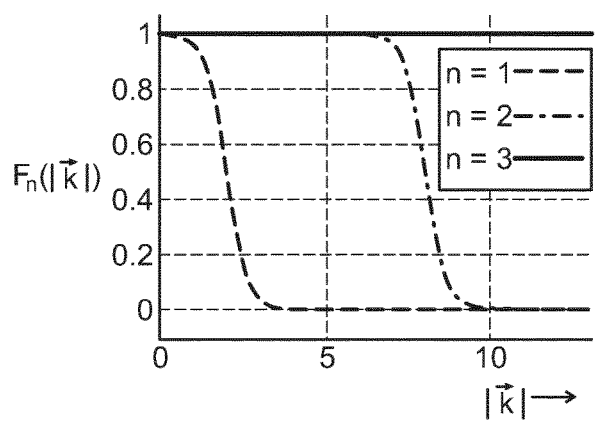
FIG. 4 shows low-pass filters according to the invention.

Finally, the sonograms of all channels are summed up, this sum is convolved with a ramp filter and back-projection interpolations are performed to obtain photo/scatter images $I_{p/s}$. A flow-chart of the method is given in FIG. 3. For filtering out unnecessary frequencies before decomposition, the x- and z-filtering commutative steps are performed before the decomposition. An example for the filters for the special case of $F_n(\vec{k})=F_n(|\vec{k}|)$ is given in FIG. 4 showing low-pass filters for the case N=3.

Figure 5:
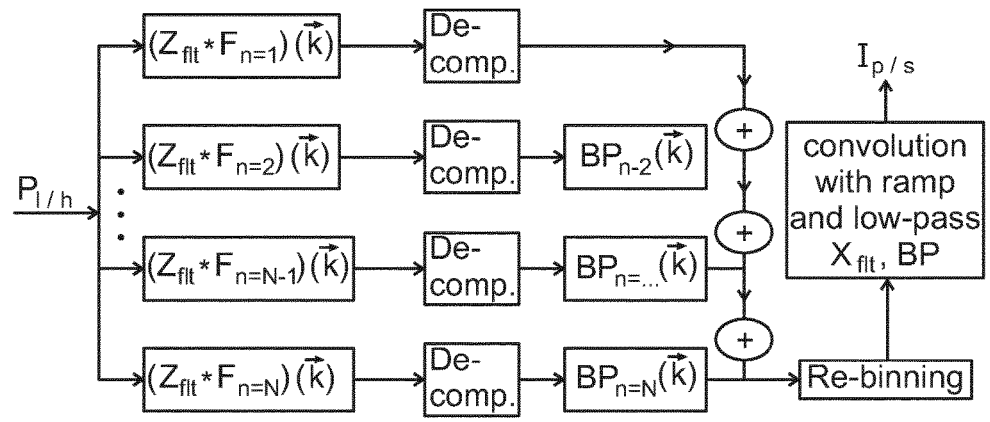
FIG. 5 shows a flow-chart of another embodiment according to the invention.

As shown in the flow-chart of FIG. 5, the method can also be implemented in a mode in which the decomposition occurs before re-binning instead of after re-binning. In other words, the re-binning, i.e. fan-to parallel and radial re-binning, can be performed after the decomposition, together with the x-filtering. Another option is that the z-filtering is postponed as well to after de-composition. In this mode, the pre-filtering is abandoned and only the split to frequency bands is left. In comparison to this mode, referring again to FIG. 3 and taking n=1, shows a mode in which the split to frequency bands is abandoned, but the pre-filtering is fully performed.

Figure 6:
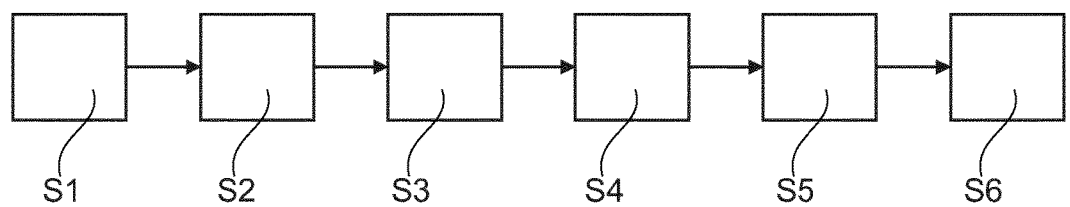
FIG. 6 shows a schematic overview of steps of an X-ray imaging method for an object.

FIG. 6 shows a schematic overview of steps of an X-ray imaging method for an object. The method comprises the following steps, not necessarily in this order:

In a first step S1, receiving attenuation data representing attenuation properties of the object for at least two different X-ray spectra.

In a second step S2, decomposing the attenuation data into decomposed data.

In a third step S3, reducing noise in the decomposed data to obtain de-noised data.

In a fourth step S4, back-converting the de-noised data into back-converted attenuation data.

In a fifth step S5, combining back-converted attenuation data and attenuation data into combined attenuation data.

In a sixth step S6, decomposing the combined attenuation data into combined decomposed data.

Figure 7:
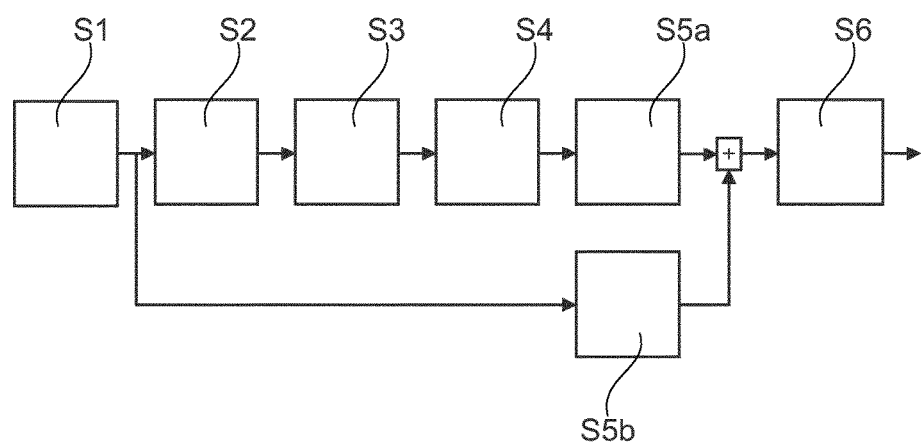
FIG. 7 shows schematically and exemplarily a further embodiment of the X-ray imaging method for an object according to the invention.

FIG. 7 shows schematically and exemplarily a further embodiment of the X-ray imaging method for an object according to the invention. In step S1, PDDN de-noised attenuation data representing attenuation properties of a scanned object are received. In step S2, these PDDN de-noised attenuation data are decomposed into decomposed data. In step S3, these decomposed data is noise reduced by means of ACF to obtain ACF de-noised data. In step S4, these ACF de-noised data are converted back to back-converted attenuation data. A frequency-split follows by a high-pass filter (step 5a) and a low-pass filter (step 5b), i.e. high spatial frequencies of back-converted ACF de-noised attenuation data are combined with low spatial frequencies of PDDN de-noised attenuation data, which results in data with less noise. In step S6, the combined high spatial frequencies of back-converted ACF de-noised attenuation data with the low spatial frequencies of PDDN de-noised attenuation data are decomposed in the second decomposition into combined decomposed data with less bias. As a result, material data with reduced noise and noise induced bias is achieved.

Figure 8:
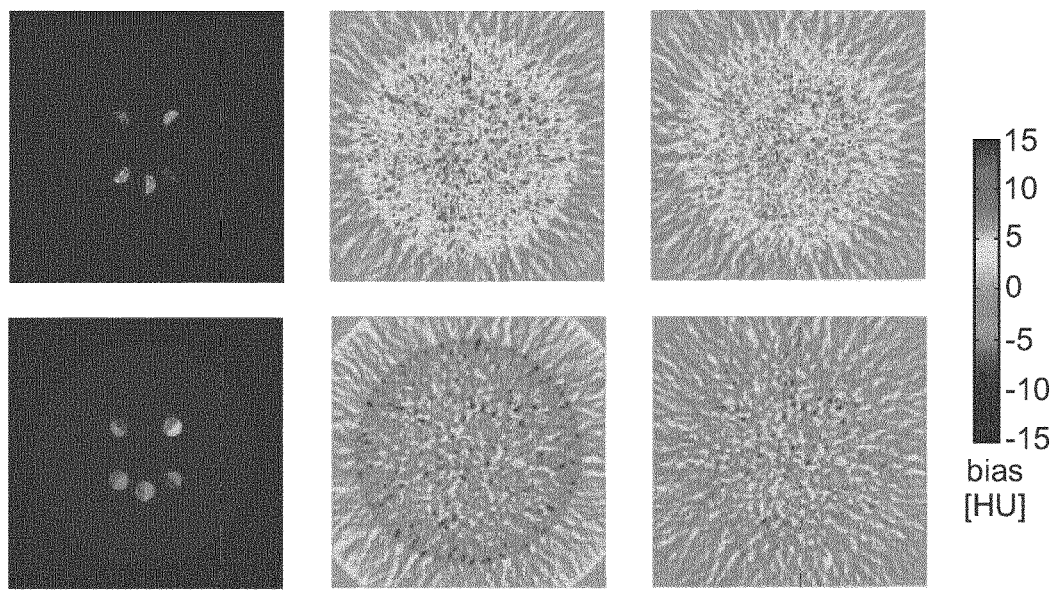
FIG. 8 shows schematically and exemplarily reconstructed material images.

FIG. 8 shows schematically and exemplarily reconstructed material images on the left, images representing bias after decomposition and ACF in the middle, and images representing bias after using the device, system or method according to the invention on the right for photo effect (upper row) and Compton scatter (lower row). As simulated phantom a 30 cm water cylinder with iodine and calcium inserts was used. The bias images are generated by subtracting images generated from noisy data from noise-free ground truth with subsequent smoothing of the difference.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging device for an object, wherein the X-ray imaging device is configured to reduce noise in input data for a spectral decomposition, the X-ray imaging device comprising a configured processor configured to:
    receive attenuation data representing attenuation properties of the object for at least two different X-ray spectra, and
    decompose the attenuation data into decomposed data,
    reduce noise in the decomposed data to obtain de-noised data,
    back-convert the de-noised data into back-converted attenuation data,
    combine back-converted attenuation data and the attenuation data into combined attenuation data, and
    decompose the combined attenuation data.

2. The X-ray imaging device according to claim 1, wherein the processor is configured to combine the back-converted attenuation data and the attenuation data into the combined attenuation data by a selection and compilation of high spatial frequencies of the back-converted attenuation data and low spatial frequencies of the attenuation data.

3. The X-ray imaging device according to claim 1, wherein the processor is configured to further reduce noise in the attenuation data before the decomposition of attenuation data into decomposed data.

4. The X-ray imaging device according to claim 1, wherein the processor is configured to reduce noise with an anti-correlation filter (ACF) and/or pre-decomposition denoising (PDDN).

5. The X-ray imaging device according to claim 1, wherein the processor is configured to combine back-converted ACF de-noised attenuation data and PDDN de-noised attenuation data into combined attenuation data by a selection and compilation of high spatial frequencies of the back-converted ACF de-noised attenuation data and low spatial frequencies of the PDDN de-noised attenuation data.

6. The X-ray imaging device according to claim 1, wherein the processor is configured to decompose in projection domain, whereby the attenuation data represent attenuation line integrals, and the processor is configured to decompose the attenuation line integrals into decomposed data representing decomposed line integrals.

7. The X-ray imaging device according to claim 1, wherein the processor is configured to decompose in image domain, whereby the attenuation data represents attenuation images, and the processor is configured to decompose the attenuation images into decomposed data representing decomposed images.

8. The X-ray imaging device according to claim 1, wherein the processor is configured to reduce noise in image domain, whereby the processor is configured to reduce noise in the decomposed images to obtain de-noised data representing de-noised images.

9. The X-ray imaging device according to claim 1, wherein the processor is configured to reduce noise in projection domain, whereby the processor is configured to reduce noise in the decomposed line integral data to obtain de-noised data representing de-noised line integrals.

10. The X-ray imaging device according to claim 1, wherein the processor is configured to reduce noise in projection domain and in image domain, whereby the noise reduction contains forward-projections and back-projections to switch between projection domain and image domain, and to reduce noise in the decomposed line integrals either in image domain or in projection domain or in both domains to obtain decomposed data representing decomposed line integrals.

11. The X-ray imaging device according to claim 1, wherein the X-ray imaging device is further configured to execute a reconstruction x- and z-filtering before decomposition.

12. The X-ray imaging device according to claim 1, wherein the X-ray imaging device is further configured to execute a low-pass filtering into different frequency ranges and to decompose the filtered data per frequency range.

13. An X-ray imaging method for an object, wherein the method comprises a noise reduction in input data for a spectral decomposition, comprising:
    receiving attenuation data representing attenuation properties of the object for at least two different X-ray spectra,
    decomposing the attenuation data into decomposed data,
    reducing noise in the decomposed data to obtain de-noised data,
    back-converting the de-noised data into back-converted attenuation data,
    combining the back-converted attenuation data and the attenuation data into combined attenuation data, and
    decomposing the combined attenuation data.

14. A non-transitory computer readable storage medium encoded with computer readable instructions, which, when executed by a processor of a computing system, causes the processor to:
    receive attenuation data representing attenuation properties of the object for at least two different X-ray spectra,
    decompose the attenuation data into decomposed data,
    reduce noise in the decomposed data to obtain de-noised data, back-convert the de-noised data into back-converted attenuation data, combine the back-converted attenuation data and the attenuation data into combined attenuation data, and decompose the combined attenuation data.

15. The computer readable storage medium of claim 14, wherein the back-converted attenuation data and the attenuation data is combined into the combined attenuation data by a selection and compilation of high spatial frequencies of the back-converted attenuation data and low spatial frequencies of the attenuation data.

16. The computer readable storage medium of claim 14, wherein noise in the attenuation data is reduced before the decomposition of attenuation data into decomposed data.

17. The computer readable storage medium of claim 14, wherein noise in the decomposed data is reduced with an anti-correlation filter (ACF) and/or PDDN.

18. The computer readable storage medium of claim 14, wherein the instructions further cause the processor to execute a reconstruction x- and z-filtering before decomposition.

\* \* \* \* \*